United States Patent
Germiquet et al.

(10) Patent No.: US 10,156,830 B2
(45) Date of Patent: Dec. 18, 2018

(54) METHOD FOR DETECTING AND CALCULATING THE DURATION OF A JUMP

(71) Applicant: The Swatch Group Research and Development Ltd, Marin (CH)

(72) Inventors: Christophe Germiquet, Preles (CH); Yvan Ferri, Lausanne (CH); Michel Willemin, Preles (CH)

(73) Assignee: The Swatch Group Research and Development Ltd, Marin (CH)

( * ) Notice: Subject to any disclaimer, the term of this patent is extended or adjusted under 35 U.S.C. 154(b) by 0 days.

(21) Appl. No.: 15/811,757

(22) Filed: Nov. 14, 2017

(65) Prior Publication Data
US 2018/0164747 A1    Jun. 14, 2018

(30) Foreign Application Priority Data
Dec. 12, 2016    (EP) .................................. 16203365

(51) Int. Cl.
*G04F 8/00*     (2006.01)
*G01P 15/18*    (2013.01)
(Continued)

(52) U.S. Cl.
CPC ............ *G04F 8/006* (2013.01); *A61B 5/1123* (2013.01); *A61B 5/681* (2013.01); *A61B 5/7282* (2013.01);
(Continued)

(58) Field of Classification Search
CPC ..... G01P 15/18; A63B 69/18; A63B 24/0062; A63B 2220/40; A63B 2220/836;
(Continued)

(56) References Cited

U.S. PATENT DOCUMENTS 5,779,576 A  *  7/1998  Smith, III .............. A63B 65/00
                                                        473/570
5,946,274 A  *  8/1999  Yamaguchi ............ G04C 3/001
                                                        307/116
(Continued)

FOREIGN PATENT DOCUMENTS

JP            2012-217584         11/2012

OTHER PUBLICATIONS

Description JP2012217584—translationportal.epo.org—Sep. 13, 2018.*
(Continued)

*Primary Examiner* — Sean P Kayes
(74) *Attorney, Agent, or Firm* — Oblon, McClelland, Maier & Neustadt, L.L.P.

(57) ABSTRACT

The invention relates to a method for detecting and calculating the duration of a jump effected by an individual, comprising the following steps:
  Detection of a moment associated with a landing following the jump, this step comprising a sub-step of detecting an acceleration peak of an amplitude greater than a first threshold amplitude, within the acceleration measurements provided by a three-axis accelerometer, on board a watch worn on the wrist of the individual.
  Detection of a jump phase, by detection, in a temporal window finishing at the moment of landing, of a succession of acceleration measurements between 0 g and 0.5 g during a duration greater than a first threshold duration.

4 Claims, 2 Drawing Sheets

(51) Int. Cl.
*A63B 24/00* (2006.01)
*A63B 69/18* (2006.01)
*A61B 5/00* (2006.01)
*A61B 5/11* (2006.01)

(52) U.S. Cl.
CPC .......... *A63B 24/0062* (2013.01); *A63B 69/18* (2013.01); *G01P 15/18* (2013.01); *A61B 2503/10* (2013.01); *A61B 2562/0219* (2013.01); *A61B 2562/0247* (2013.01); *A63B 2069/185* (2013.01); *A63B 2220/40* (2013.01); *A63B 2220/44* (2013.01); *A63B 2220/62* (2013.01); *A63B 2220/836* (2013.01)

(58) Field of Classification Search
CPC ............ A63B 2220/44; A63B 2220/62; A63B 2069/185; A61B 5/7282; A61B 5/1123; A61B 5/681; A61B 2503/10; A61B 2562/0219; A61B 2562/0247; G04F 8/006
See application file for complete search history.

(56) References Cited

U.S. PATENT DOCUMENTS

| | | | | |
|---|---|---|---|---|
| 6,018,705 A * | 1/2000 | Gaudet | ................ | A61B 5/1121 235/105 |
| 6,167,356 A * | 12/2000 | Squadron | ................ | A63B 5/16 702/141 |
| 6,493,652 B1 * | 12/2002 | Ohlenbusch | ......... | A61B 5/1038 324/160 |
| 7,379,842 B2 * | 5/2008 | Alexander | ......... | A63B 24/0021 702/160 |
| 7,650,257 B2 * | 1/2010 | Alexander | ......... | A63B 24/0021 702/150 |
| 8,108,177 B2 * | 1/2012 | Alexander | ......... | A63B 24/0021 702/141 |
| 9,055,164 B2 * | 6/2015 | Hasegawa | .............. | G04C 3/002 |
| 2006/0031039 A1 * | 2/2006 | Flentov | .................... | A61B 5/11 702/141 |
| 2015/0153374 A1 * | 6/2015 | Balakrishnan | .......... | G01P 13/00 702/178 |

OTHER PUBLICATIONS

European Search Report dated Jun. 14, 2017 in European Application 16203365.8, filed on Dec. 12, 2016 (with English Translation of Categories of cited documents).

Tien Jung Lee, et al. "Automatic jump detection in skiing/snowboarding using head-mounted MEMS inertial and pressure sensors", Proceedings of the Institution of Mechanical Engineers, Part P: Journal of Sports Engineering and Technology, vol. 229, No. 4, XP008184828, 2015, 10 pages.

Claire L. Roberts-Thomson, et al. "Jump Detection Using Fuzzy Logic", 2014 IEEE Symposium on Computational Intelligence for Engineering Solutions (CIES), XP032723870, 2014, 7 pages.

* cited by examiner

METHOD FOR DETECTING AND CALCULATING THE DURATION OF A JUMP

This application claims priority from European Patent Application No. 16203365.8 filed on Dec. 12, 2016, the entire disclosure of which is hereby incorporated herein by reference.

FIELD OF THE INVENTION

The invention relates to a method for detecting and calculating the duration of a jump. The method is adapted to jumps which use travel means making it possible to take a run-up before the jump, such as skis, a snowboard, rollerblades, a bicycle, a skateboard, etc. The method is likewise adapted to jumps which do not use this type of travel means, for example jumps into water, from a cliff, a diving board or a bridge.

There is meant, by duration, the difference between the moment of landing and the moment when the athlete starts the jump. In the case of a jump into water, the entry of the athlete into the water is called the landing.

BACKGROUND OF THE INVENTION

There is known, from document US 2002/0116147, a method for detecting and analyzing a jump by means of a measuring unit mounted on travel means used by an athlete for taking a run-up before the jump and being situated in contact with the ground before and after the jump. The travel means are for example skis or a snowboard. A calculation unit, for example a watch worn by the athlete, makes it possible to determine and to display parameters of the jump, in particular the duration of the jump, from measurements produced by the measuring unit. More precisely, the measuring unit picks up vibrations of the travel means in order to detect when the travel means leave the ground and return to the ground, which makes it possible to detect a jump and to calculate the duration thereof.

This method has the disadvantage of requiring the use of a measuring unit to be fixed to the travel means in order to measure the vibrations to which they are subjected. Furthermore, the method does not make it possible to calculate the duration of a jump effected without travel means in contact with the ground before or after the jump, for example a jump into water from a cliff.

SUMMARY OF THE INVENTION

The aim of the present invention is to remedy all or part of the previously cited disadvantages.

To this end, the invention relates to a method for detecting and calculating the duration of a jump effected by an individual, comprising the following steps:
  detection of a moment associated with a landing following the jump, this step comprising a sub-step of detecting an acceleration peak of an amplitude greater than a first threshold amplitude, within the acceleration measurements provided by a three-axis accelerometer, on board a watch worn on the wrist of the individual,
  detection of a jump phase, by detection, in a temporal window finishing at the moment of landing, of a succession of acceleration measurements between 0 g and 0.5 g during a duration greater than a first threshold duration.

There is meant by g, the acceleration due to gravity at the Earth's surface: $9.80665 \; m \cdot s^{-2}$.

There is meant, by acceleration measurement, the norm of a 3-component acceleration vector, i.e. the square root of the sum of the squares of the components.

The invention benefits from acknowledgement that a landing on the ground or in the water following a jump is the cause of a strong acceleration peak observed within the data measured by a triaxial accelerometer. Detection of an acceleration peak is therefore an indication that a jump has been effected. In order to confirm that a jump has indeed been effected and that the acceleration peak does not correspond to a false detection, the acceleration measurements preceding the acceleration peak are analyzed. In fact, during a jump, the individual is in free fall, therefore the norm of his acceleration is in theory zero. A succession of acceleration measurements near to zero during a duration which is sufficiently long, followed by a sufficiently large acceleration peak, indicates therefore that a jump has been effected.

Besides that, the method comprises the following steps:
  Detection of a moment associated with the start of the jump corresponding to the first measurement of the succession of acceleration measurements between 0 g and 0.5 g.
  Calculation of a duration of the jump by the difference of the moment associated with the landing and the moment associated with the start of the jump.

When a jump phase has been detected, the acceleration measurements are used to calculate the duration of the jump. The first measurement of the successive acceleration measurements between 0 and 0.5 g corresponds to the moment when the individual started the jump. As for the acceleration peak, it corresponds to the moment when the individual has landed. By subtracting the first measurement and the moment of the acceleration peak, the duration of the jump can therefore be calculated.

Furthermore, the step of detecting a moment associated with a landing comprises a sub-step of detecting a pressure peak of an amplitude greater than a second threshold amplitude and of lesser duration than a second threshold duration, from pressure measurements provided by a pressure sensor on board the watch, and a sub-step of comparing the moment associated with the acceleration peak and the moment associated with the pressure peak.

The aforementioned features benefit from acknowledgment that a landing following a jump is the cause of a strong pressure peak observed within the data measured by a pressure sensor. Detection of a pressure peak is therefore an indication of a landing which makes it possible to confirm that a jump has in fact taken place by correlation with the acceleration peak.

Apart from the aforementioned features, the method according to the invention may comprise the following features, taken alone or in combination according to all technically possible combinations.

In a non-limiting embodiment, the second threshold amplitude is greater than 2 millibars and the second threshold duration is greater than 0.1 second.

In a non-limiting embodiment, the first threshold duration is greater than 0.5 second.

In a non-limiting embodiment, the first threshold amplitude is greater than 2 g.

BRIEF DESCRIPTION OF THE DRAWINGS

Other features and advantages will emerge clearly from the description which is given hereafter, by way of indication and in no way limiting, with reference to the annexed drawings, in which.

DETAILED DESCRIPTION OF PREFERRED EMBODIMENTS

Figure 1:
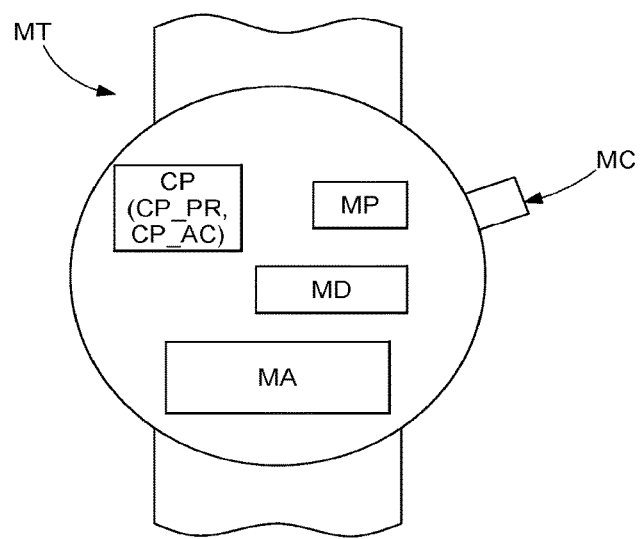
FIG. 1 represents an electronic watch making is possible to implement the method according to one embodiment of the invention.

The method METH according to the invention is implemented integrally by an electronic watch MT worn by an individual making a jump. In a non-limiting embodiment shown in FIG. 1, the watch MT comprises:
- a set of sensors CP, comprising an accelerometer CP_AC and a pressure sensor CP_PR (or altimeter)
- a memory MD for recording measurements produced by the sensors CP. The measurements are advantageously recorded in the memory in a sliding manner, according to the FIFO principle ("first in, first out")
- a microprocessor MP for processing the information contained in the memory MD
- digital or analogue display means MA for displaying the results of the calculations produced by the microprocessor MP
- activation means MC, mechanical, electronic or tactile, of the sensors CP, of the memory MD, of the microprocessor MP and of the display means MA, making it possible to trigger the method PR.

Figure 2:
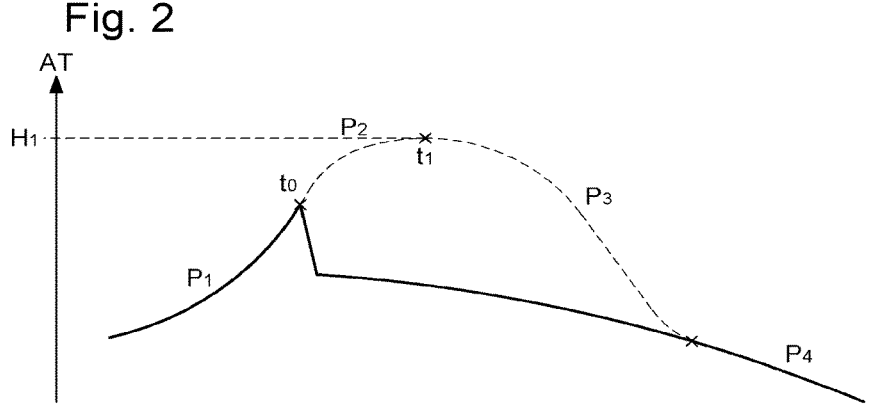
FIG. 2 illustrates an example of the trajectory of a ski jump.

FIG. 2 shows an example of the trajectory of a jump, occurring during a ski jump. In a first phase $P_1$, the individual is in contact with the ground. At a time $t_0$, the individual takes off from the ground, and in a second phase $P_2$, the individual is in the rising phase. At a time $t_1$, the individual reaches a maximum altitude $H_1$ and, in a third phase $P_3$, the individual is in a descending phase. At a time $t_2$, the individual lands on the ground, and in a fourth phase $P_4$, the individual is again in contact with the ground.

Figure 3:
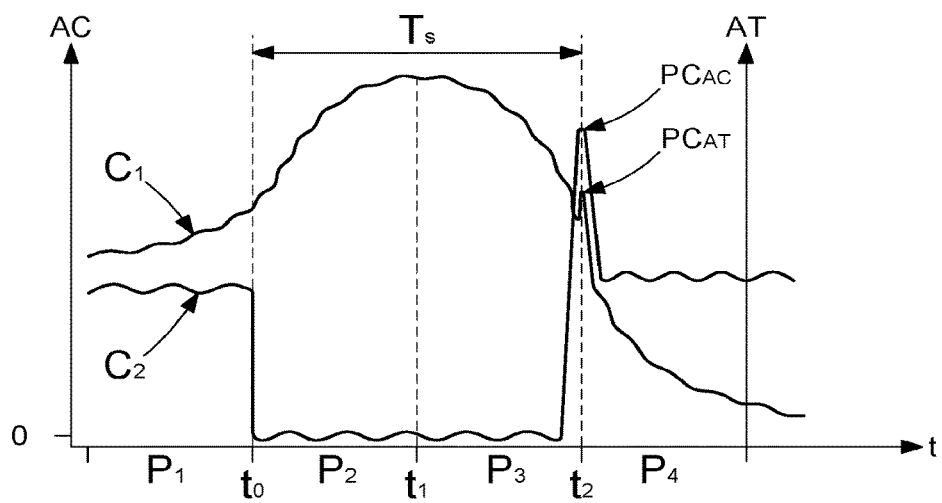
FIG. 3 shows a curve representing acceleration measurements, superimposed on a curve representing pressure measurements, the measurements being produced during the jump of FIG. 2.

FIG. 3 shows a curve $C_1$ representing the altitude measurements AT calculated from the pressure measurements picked up by the pressure sensor CP_PR of the watch MT, as a function of the time t, and in particular during the four phases $P_1$, $P_2$, $P_3$ and $P_4$. A curve $C_2$ representing the acceleration AC measured by the accelerometer CP_AC of the watch MT as a function of the time t, is superimposed on the altitude curve $C_1$.

Figure 4:
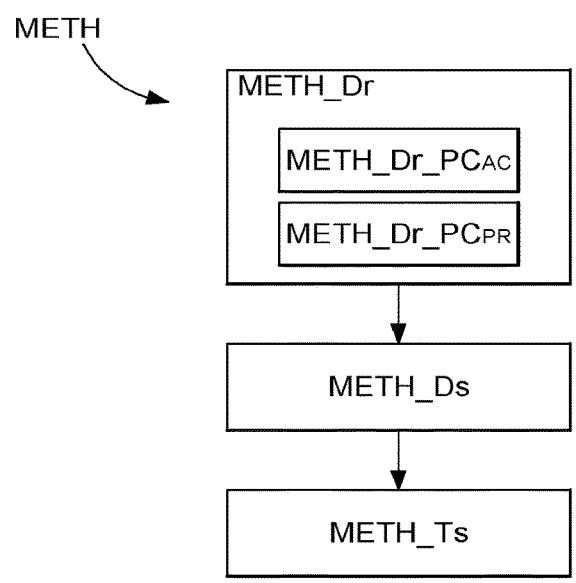
FIG. 4 shows a functional diagram which is representative of the steps of the method.

A first step of the method METH according to the invention consists of detecting that a jump has been effected (step METH_Dr in FIG. 4). More particularly, the detection step METH_Dr comprises a first sub-step METH_Dr_$PC_{AC}$ consisting of detecting an acceleration peak $PC_{AC}$ in the measurements provided by the accelerometer CP_AC. In fact, when a jump is effected, an acceleration peak $PC_{AC}$ is observed at the moment $t_2$, i.e. upon the individual landing on the ground. When such a peak $PC_{AC}$ is detected, it is compared to a threshold value beyond which it is decided that the peak $PC_{AC}$ corresponds in fact to a landing on the ground following a jump.

In one embodiment, in order to confirm that this acceleration peak $PC_{AC}$ in fact corresponds to a landing following a jump, the detection step METH_Dr likewise comprises a second sub-step METH_Dr_$PC_{PR}$ consisting of detecting a pressure peak $PC_{PR}$ in the measurements provided by the pressure sensor CP_PR. The corresponding altitude peak $PC_{AT}$ is represented in FIG. 3. If a jump has in fact taken place, such a pressure peak $PC_{PR}$ should be picked up at a moment which is substantially identical to that at which the acceleration peak $PC_{AC}$ was detected. The moments corresponding to the pressure peak $PC_{PR}$ and to the acceleration peak $PC_{AC}$ are therefore compared. If the norm of the difference between these moments is less than a threshold value, for example 0.5 second, then it is decided that the peaks $PC_{PR}$, $PC_{AC}$ correspond in fact to a landing on the ground following a jump.

A second step of the method METH according to the invention consists of detecting a jump phase (step METH_Ds), by detection, in a temporal window finishing at the previously determined moment $t_2$, of a succession of acceleration measurements AC between 0 g and 0.5 g during a duration greater than a first threshold duration $t_S$. For this, the acceleration measurements AC in a temporal window preceding the acceleration peak $P_{AC}$, for example a temporal window of about ten seconds, are analysed. More precisely, the step METH_Ds for detecting a jump phase comprises calculation of the norms of the acceleration measurements of the temporal window. It is therefore possible to determine if the acceleration peak $PC_{AC}$ is preceded by a succession of measurements between 0 g and 0.5 g during a duration greater than the first threshold duration $t_S$. If this is the case, it is confirmed that a jump has in fact taken place and that the acceleration peak $PC_{AC}$ corresponds to a landing on the ground. In fact, during the third phase $P_3$, the individual is in free fall and therefore undergoes an acceleration of approximatively 0 g. The first of the succession of measurements between 0 g and 0.5 g corresponds to a time $t_0$ attributed to the start of the jump.

In a third step of the method, the duration Ts of the jump is calculated (step METH_Ts). For this, the moment $t_2$ associated with the landing is subtracted from the moment $t_0$ associated with the start of the jump.

It is noted therefore that the step METH_Ds for detecting a jump phase contributes not only to confirming that a jump has in fact taken place but likewise to calculating the duration of this jump.

Of course, the present invention is not limited to the illustrated example but is applicable to different variants and modifications which will appear to the person skilled in the art.

What is claimed is:

1. A method for detecting and calculating the duration of a jump effected by an individual, comprising the following steps:
   - detection of a moment associated with a landing following the jump, this step comprising a sub-step of detecting an acceleration peak of an amplitude greater than a first threshold amplitude, within the acceleration measurements provided by a three-axis accelerometer, on board a watch worn on the wrist of the individual,
   - detection of a jump phase, by detection, in a temporal window finishing at the moment of landing, of a succession of acceleration measurements between 0 g and 0.5 g during a duration greater than a first threshold duration, g being the acceleration due to gravity at the Earth's surface,
   - detection of a moment associated with the start of the jump corresponding to the first measurement of the succession of acceleration measurements between 0 and 0.5 g, calculation of a duration of the jump by the difference of the moment associated with the landing and the moment associated with the start of the jump, the step of detecting a moment associated with a landing comprising a sub-step of detecting a pressure peak of an amplitude greater than a second threshold amplitude and of lesser duration than a second threshold duration, from pressure measurements provided by a pressure sensor on board the watch, and a sub-step of comparing the moment associated with the acceleration peak and the moment associated with the pressure peak.

2. The method according to claim 1, in which the second threshold amplitude is greater than 2 millibars and the second threshold duration is less than 0.1 second.

3. The method according to claim 1, in which the first threshold duration is greater than 0.5 second.

4. The method according to claim 1, in which the first threshold amplitude is greater than 2 g.

* * * * *